United States Patent [19]

Newhall

[11] 3,960,539

[45] June 1, 1976

[54] LIMONENE DERIVATIVES USED IN GROWTH INHIBITION AND PLANT ABSCISSION PROCESSES

[75] Inventor: William F. Newhall, Winter Haven, Fla.

[73] Assignee: Amchem Products, Inc., Ambler, Pa.

[22] Filed: Aug. 3, 1970

[21] Appl. No.: 60,717

Related U.S. Application Data

[60] Division of Ser. No. 825,437, May 16, 1969, Pat. No. 3,564,046, which is a continuation-in-part of Ser. No. 604,622, Dec. 27, 1966, abandoned.

[52] U.S. Cl. .............................. 71/76; 71/70; 71/71; 71/72; 71/74; 71/86; 71/94; 71/95; 71/103; 71/106; 71/107; 71/111; 71/121

[51] Int. Cl.$^2$............................ A01N 9/24

[58] Field of Search ............ 71/121, 94, 76, 70, 71/71, 72, 86

[56] References Cited
UNITED STATES PATENTS 3,397,053    8/1968    Bordenca et al.............. 71/121

OTHER PUBLICATIONS

Krewson et al., J. Arg. Food Chem. 7, 264–268 (1959).

Newhall et al., J. Agr. Food Chem. 14, No. 1, 1966 (23–27).

Pieringer et al., J. Agr. Food Chem. 16, No. 3 6/68, 523, 524.

*Primary Examiner*—Lewis Gotts
*Assistant Examiner*—Catherine L. Mills
*Attorney, Agent, or Firm*—Caesar, Rivise, Bernstein & Cohen, Ltd.

[57] ABSTRACT

Uses of Limonene Derivatives involving chemical compositions of the quaternary ammonium type as derived from limonene, possess plant growth regulant, nematocidal and fungicidal properties. They are suitable for use at concentrations varying from as little as several parts per million parts of carrier, to as much as several thousand parts per million parts of carrier. Compositions useful in the present invention are exemplified by benzyl dimethyl (1-hydroxy-p-menth-8-en-2-yl) ammonium chloride; but many other compounds of somewhat different character are contemplated.

4 Claims, No Drawings

LIMONENE DERIVATIVES USED IN GROWTH INHIBITION AND PLANT ABSCISSION PROCESSES

This application is a divisional application based on pending Application Ser. No. 825,437, filed May 16, 1969 now U.S. Pat. No. 3,564,046 and entitled "Limonene Derivatives and Uses Thereof" which was a Continuation-In-Part application based on application Ser. No. 604,622, filed Dec. 27, 1966 now abandoned and entitled "Quaternary Ammonium Derivatives from Limonene".

The present invention relates to uses of novel and useful quaternary ammonium compounds derived from limonene.

The object of the present invention is the use of compounds possessing plant growth regulant, nematocidal and fungicidal activity.

A further object of the present invention is the use of new compounds and methods for regulating plant growth.

A concomitant object of the present invention is the use of new compounds and methods for controlling fungi.

Yet another object of this invention is a use of new compounds and methods for controlling nematodes.

The present invention pertains to the regulation of plant growth and the control of nematodes and fungi by the use of structure

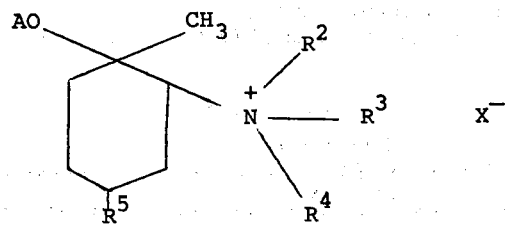

wherein:

A is selected from the group consisting of hydrogen and

wherein $R^1$ is selected from the group consisting of alkyl groups of from 1 to 4 total carbon atoms, aryl groups and substituted aryl groups wherein the substituents may be halogen, nitro, amino, hydroxy, and alkyl and alkoxy groups of from 1 to 4 carbon atoms;

$R^2$ is selected from the group consisting of alkyl groups of from 1 to 4 total carbon atoms;

$R^3$ is selected from the group consisting of alkyl groups of from 1 to 4 total carbon atoms, and when taken together with $R^2$, constitutes part of a heterocyclic ring having from 5 to 6 members;

$R^4$ is selected from the group consisting of hydrogen, alkyl of 1 to 18 carbon atoms, cycloalkyl of 3 to 8 carbon atoms, alkenyl groups of 2 to 18 carbon atoms, and aralkyl in which the aryl moiety is substituted by one or more substituents selected from the group consisting of halo, nitro, amino, hydroxy and alkyl (1 to 4 total carbon atoms) substituents thereof; and $R^5$ is selected from the group consisting of propyl and propenyl.

X is the anionic moiety of any suitable organic or inorganic acid such as an acid anion selected from the group consisting of halides, sulfates, phosphates, sulfonates and alkanoates of from 1 to 8 total carbon atoms.

In this product aspect the invention pertains to the use of compounds as described above with the further proviso that when A is hydrogen at least one of $R_2$, $R_3$ or $R_4$ is other than methyl.

The compounds used in this invention can be present as sterioisomers and it is intended to include both position isomers and trans forms as well as mixtures thereof.

The terms alkyl and alkenyl as used herein connote both straight and branched chain hydrocarbons. In particular the terms propyl and propenyl include also the isopropyl and isopropenyl groups with isopropyl being preferred. The preferred halides are the chlorides, bromides and iodides with chloride and bromide being especially preferred. The term aralkyl as used herein connotes monocyclic aromatic alkyl groups wherein the alkyl group contains 1 to 3 carbon atoms and the aromatic group is phenyl or phenyl substituted by one or more functional groups such as halo, nitro, amino, hydroxy or alkyl (e.g. phenyl, phenethyl). Preferred halo groups are chloro and bromo. When $R^4$ is alkyl the preferred groups are the alkyl of 5 to 10 carbon atoms. Particularly preferred compounds are the quaternary salts of the above formula wherein A is hydrogen, $R_5$ is isopropyl or isopropenyl, $R_2$ and $R_3$ are each methyl, $R_4$ is aralkyl as defined above, cycloalkyl of 5 or 6 carbon atoms or alkyl or 2 to 18 carbon atoms, and X is as defined above.

These compounds used in this invention display properties which are useful in agricultural art such, for example, as fungicides, nematocides and plant growth regulants.

Typical but non-limited examples of compounds used in this invention include:

| EXAMPLE | COMPOUND |
|---|---|
| 1 | benzyl dimethyl (1-hydroxy-p-menth-8-en-1-ol) ammonium chloride |
| 2 | 2-dimethylamino-p-menth-8-en-1-ol, hydrochloride |
| 3 | 2-dimethylamino-p-menth-8-en-1-ol, sulfate |
| 4 | benzyl, diisopropyl )1-hydroxy-p-menth-8-en-2-yl) ammonium chloride |
| 5 | 2-diisopropylamino-p-menth-8-en-1-ol, hydroiodide |
| 6 | 2-diethylamino-p-menth-8-en-1-ol, hydrobromide |
| 7 | 2-diethylamino-p-menth-8-en-1-ol, hydrofluoride |
| 8 | 4-chlorobenzyl, dimethyl (1-hydroxy-p-menth-8-en-2-yl) ammonium chloride |
| 9 | 2-(isoproylmethylamino)-p-menth-8-en-1-ol, hydrochloride |

| EXAMPLE | COMPOUND |
|---|---|
| 10 | 2-(butylmethylamino)-p-menth-8-en-1-ol, hydroiodide |
| 11 | 4-chlorobenzyl diethyl (1-hydroxy-p-menth-8-en-2-yl) ammonium chloride |
| 12 | 2,4-dichlorobenzyl diethyl (1-hydroxy-p-menth-8-en-2-yl) ammonium chloride |
| 13 | 2,4-dichlorobenzyl dimethyl (1-hydroxy-p-menth-8-en-2-yl) ammonium chloride |
| 14 | dimethyl (1-hydroxy-p-menth-8-en-2-yl) 2,3,6-trichlorobenzylammonium chloride |
| 15 | 2-dimethylamino-p-menth-8-en-1-ol, acetate |
| 16 | 2-dimethylamino-p-menth-8-en-1-ol, phosphate |
| 17 | 1-(1-hydroxy-p-menth-8-en-2-yl) 1-methylpiperidinium iodide |
| 18 | 1-(1-hydroxy-p-menth-2-yl) 1-methylpiperidinium iodide |
| 19 | 4-chlorobenzyl dimethyl (1-hydroxy-p-menth-2-yl) ammonium chloride |
| 20 | 4-chlorobenzyl diisopropyl (1-hydroxy-p-menth-2-yl) ammonium chloride |
| 21 | 4-chlorobenzyl (1-hydroxy-p-menth-2-yl) isobutyl methylammonium chloride |
| 22 | 2-dimethylamino-p-menthan-1-ol, nitrate |
| 23 | 2-dimethylamino-p-menthan-1-ol, p-toluene sulfonate |
| 24 | 2-dimethylamino-p-menthan-1-ol, propionate |
| 25 | 2-dimethylamino-p-menthan-1-ol, isobutyrate |
| 26 | (2,4-dichlorobenzyl) dimethyl (1-hydroxy-p-menth-2-yl) ammonium chloride |
| 27 | 2-dimethylamino-p-menth-8-en-1-ol, 6-methylheptanate |
| 28 | 2-(butylethylamino)-p-menth-8-en-1-ol, diethylphosphonate |
| 29 | 2-dimethylamino-p-menthan-1-ol formate |
| 30 | 2-dimethylamino-p-menthan-1-ol acetate |

The compounds used in the present invention range from colorless liquids to colorless to pale yellow amorphous glasses or solids. In general, they are prepared by reacting an animo alcohol with the desired alkyl or aryl halide under reflux conditions. Recovery of the desired products is accomplished utilizing accepted techniques of concentration under reduced pressure followed by purification using washing and/or recrystallization procedures.

The quaternary ammonium compounds and acid salts of tertiary amines used in the present invention are soluble in water and in polar organic solvents such as alcohols and ketones. The degree of water solubility of these compounds varies from several percent to very high levels of up to 70–80%. Accordingly, the use of imple aqueous solutions of these compounds for the control of plant growth or of nematodes or fungi is readily accomplished by water solutions thereof.

The amino alcohols utilized as intermediates to prepare the quaternary compounds used in the present invention are synthesized according to the methods of W. F. Newhall as published in J. Org. Chem., 24, 1673 (1959) and in J. Org. Chem., 29, 185 (1964).

The invention is further illustrated by the following examples which are presented solely by way of illustration and which are not intended to limit this invention. All temperatures given in these examples are presented in degrees of centigrade, unless otherwise stated.

EXAMPLE 31 benzyl dimethyl (1-hydroxy-p-menth-8-en-2-yl) ammonium chloride

Ten grams of the mixed isomers of 2-dimethylamino-Δ 8 (9)-p-menthen-1-ol were dissolved in 25 ml. of methyl ethyl ketone and 20 ml. of benzyl chloride was added. The resulting solution was refluxed for 70 hours. Most of the methyl ethyl ketone was removed at reduced pressure using a film evaporator (water bath temperature 50°). Fifty ml. of water were added to the flask and the mixture was transferred to a separatory funnel. The aqueous phase was washed five times with ethyl ether and the ether washes were discarded. Concentration of the aqueous phase at reduced pressure afforded 12.65 g. (77% of theoretical yield) of benzyl dimethyl (1-hydroxy-p-menth-8-en-2-yl) ammonium chloride as a colorless, amorphous glass.

Anal. Calc'd for $C_{19}H_{30}NOCl$: N,4.33. Found: N,4.35.

EXAMPLE 32

4-chlorobenzyl dimethyl (1-hydroxy-p-menth-8-en-2-yl) ammonium chloride

Ten grams of the mixed isomers of 2-dimethylamino-Δ 8 (9)-p-menthen-1-ol were dissolved in 25 ml. of methyl ethyl ketone and 20 ml. of p,α-dichlorotoluene was added. The resulting solution was refluxed for 70 hours. Most of the methyl ethyl ketone was removed at reduced pressure using a film evaporator (water bath temperature 50°). One hundred ml. of water were added to the flask and the mixture was transferred to a separatory funnel. The aqueous phase was washed five times with ethyl ether and the other washes were discarded. Concentrations of the aqueous phase at reduced pressure afforded 14.75 (81% of theoretical yield) of 4-chlorobenzyl dimethyl (1-hydroxy-p-menth-8-en-2-yl) ammonium chloride as a colorless, amorphous glass.

Anal. Calc'd for $C_{19}H_{29}NOCl_2$: N,3.91 Found: H,3.95.

EXAMPLE 33

2,4-dichlorobenzyl dimethyl (1-hydroxy-p-menth-8-en-2-yl) ammonium chloride

Ten grams of the mixed isomers of 2-dimethylamino-Δ 8 (9)-p-menthen-1-ol were dissolved in 25 ml. of methyl ethyl ketone and 20 ml. of α,2,4-dichlorotoluene was added. The resulting solution was refluxed for 70 hours. Most of the methyl ethyl ketone was removed at reduced pressure using a film evaporator (water bath temperature 50°). Three hundred ml. of water were added to the flask and the mixture was transferred to a separatory funnel. The aqueous phase was washed five times with ethyl ether and the ether washes were discarded. Concentration of the aqueous phase at reduced pressure afforded 8.73 g. (44% of theoretical yield) of 2,4-dichlorobenzyl dimethyl (1-hydroxy-p-menth-8-en-2-yl) ammonium chloride.

Anal. Calc'd. for $C_{19}H_{28}NOCl_3$: N,3.57. Found: N,3.73.

Example 34 benzyl dimethyl (1-hydroxy-p-menth-2-yl) ammonium chloride

Five grams of the mixed isomers of 2-dimethylamino-1-p-menthanol were dissolved in 25 ml. of methyl ethyl ketone and 10 ml. of benzyl chloride was added. The resulting solution was refluxed for 70 hours. Most of the methyl ethyl ketone was removed at reduced pressure using a film evaporator (water bath temperature 50°). Fifty ml. of water were added to the flask and the mixture was transferred to a separatory funnel. The aqueous phase was washed five times with ethyl ether and the ether washes were discarded. Concentration of the aqueous phase at reduced pressure afforded 6.6 g. (81% theoretical yield) of benzyl dimethyl (1-hydroxy-p-menth-2-yl) ammonium chloride as a colorless, amorphous glass.

Anal. Calc'd for $C_{19}H_{32}NOCl$: N,4.29. Found: N,3.91.

EXAMPLE 35

2,4-dichlorobenzyl dimethyl (1-hydroxy-p-menth-2-yl) ammonium chloride

Five grams of the mixed isomers of 2-dimethylamino-1-p-menthanol were dissolved in 25 ml. of methyl ethyl ketone and 10 ml. of $\alpha$,2,4-trichlorotoluene was added. The resulting solution was refluxed for 70 hours. Most of the methyl ethyl ketone was removed at reduced pressure using a film evaporator (water bath temperature 50°). Three hundred ml. of water were added to the flask and the mixture was transferred to a separatory funnel. The aqueous phase was washed five times with ethyl ether and the ether washes were discarded. Concentration of the aqueous phase at reduced pressure afforded 3.44 g. (35% of theoretical yield) of 2,4-dichlorobenzyl dimethyl (1-hydroxy-p-menth-2-yl) ammonium chloride.

Anal. Calc'd for $C_{19}H_{30}NOCl_3$: N,3.55. Found: N,3.33.

EXAMPLE 36 dimethyl heptyl (1-hydroxy-p-menth-2-yl) ammonium bromide

Five grams of the mixed isomers of 2-dimethylamino-1-p-menthanol were dissolved in 10 ml. of methyl ethyl ketone and 10 g. of heptyl bromide added. The resulting solution was refluxed for 72 hours. Most of the methyl ethyl ketone was removed at reduced pressure using a film evaporator (water bath temperature 50°). Five hundred ml. of water were added to the flask and the mixture was transferred to a separatory funnel. The aqueous phase was washed five times with ethyl ether and the ether washes were discarded. Concentration of the aqueous phase at reduced pressure afforded 6.53 g. (65% of theoretical yield) of dimethyl heptyl (1-hydroxy-p-menth-2-yl) ammonium bromide.

Anal. Calc'd for $C_{19}H_{40}NOBr$: N,3.70. Found: 3.69.

In similar manner, a number of homologs of the compounds described in the examples have been prepared and found to be effective as plant growth regulants, fungicides, and/or nematocides. As will now be understood by those skilled in the art, these compounds were all synthesized by the same general method from readily available raw materials.

Depending upon the ultimate use of the compounds used in this invention, that is whether they are to be employed as plant growth regulants, as fungicides or as nematocides, greater or lesser amounts of a respective compound will be used. Suffice it to say that notwithstanding the desired ultimate use, an amount of compound, falling within the scope of this invention, of between 0.01 and 10% by weight of total composition will provide the desired results.

In order to illustrate various properties displayed by the compounds used in this invention, there are presented below additional examples which are presented solely by way of illustration and are not in any way intended to be construed as a limitation of this invention.

EXAMPLE 37

Twenty-four grapefruit seedlings (Approx. 8 inches high) growing in sandy, steam sterilized soil were divided into four groups of six plants. The following applications were made:
A. No treatment
B. No treatment
C. Soil drench, using 100 ml. of an aqueous solution containing 3000 ppm. of the compound of Example 13.
D. Lanolin paste containing a 1% concentration of the compound of Example 13.

After 8 days all plants were removed from the pots and the roots washed. Roots of all plants from groups B, C and D were suspended in an aqueous suspension of zoospores (*Phytophthera parasitica*).

Group A plants were suspended in water without zoospores. All of these plants were then replanted in sandy, steam sterilized soil.

After approximately 2 months additional growth, visual observations of the roots of all the treated plants indicated stimulation of root development occured as a result of treatment by the chemical.

Non-inoculated controls (Group A) — normal root development — healthy appearance with short new root growth developing at tips of existing roots.

Non-treated inoculated controls (Group B) — some new root growth mostly near crown. All original roots dead.

Soil drench (Group C) — several plants produced exceedingly vigorous roots.

Lanolin paste (Group D) — majority of plants produced abundant amounts of new and exceedingly vigorous roots.

EXAMPLE 38

Leaf abscission was demonstrated utilizing the compounds of Examples 1 and 26, as identified above, in the following manner. Twenty-four grapefruit seedling plants, growing in individual containers of sandy, steam sterilized soil, were divided into three groups, of 8 plants each. One hundred ml. of an aqueous solution containing 3000 ppm. of the compound of Example 1 was applied to the soil of each of these plants in all three groups. This application was repeated after a 30-day interval on two of these groups, and was again repeated after an additional 30-day interval on only one of the groups.

After 5 days, the only nematodes still alive were 4 in the 0.001% and 9 in the deionized water control. These results are summarized below.

| Conc. of Compound of Example 13 | Percent of Nematodes 24 hours | (of orig. 10) 48 hours | Surviving After 5 days |
|---|---|---|---|
| 0.1% | 0 | 0 | 0 |
| 0.01% | 40 | 0 | 0 |
| 0.001% | 100 | 80 | 40 |
| Control (water) | 100 | 100 | 90 |

Twenty-four additional grapefruit seedlings, growing in individual containers of sandy, steam sterilized soil, were separated into three groups of eight plants each and were treated similarly with aqueous solutions containing 3000 ppm. of the compound of Example 26 as reported above.

With respect to treatment with the compounds of both Examples 1 and 26, it was observed that older leaves abscissed on plants which had been subjected to the second and third treatments, such abscission occurring about 1 week following the respective treatments. No abscission was observed on plants which received only one treatment.

EXAMPLE 39

Fruit abscission was demonstrated utilizing Hamlin oranges with 4 to 5 inch stems attached. The fruit was supported on a screen with the stems projecting downward into an aqueous solution of a compound of this invention. Abscission, as reported in the following table, was observed by separation of the fruit from the stem and button:

| Compound of Example No. | Concentration Molar | % abscission after - 48 hrs. | 72 hrs. | 96 hrs. |
|---|---|---|---|---|
| Water (control) | — | 0 | 0 | 20 |
| 19 | $10^{-3}$ | 5 | 55 | 100 |
| 19* | $10^{-3}$ | 0 | 20 | 100 |
| 26 | $10^{-3}$ | 0 | 50 | 90 |
| 34 | $10^{-3}$ | 5 | 20 | 93 |
| 34 | $10^{-2}$ | 100 | — | — |

*Acetate ester of the compound of Example 19.

EXAMPLE 40

Nematocidal activity of compounds of the present invention is illustrated by the following test:

Ten active burrowing nematodes [*Radopholus Similis* (Cobb) Thorne 1949] were exposed to concentrations of 0.1%, 0.01% and 0.001% of the compound of Example 13 in deionized water. All tests were conducted in small Syracuse dishes.

At the end of 24 hours, all burrowing nematodes were dead in the 0.1% solution, 6 of 10 were dead in the 0.01% solution, and none were dead in either the 0.001% solution or in the control with deionized water.

After 48 hours all nematodes in the 0.01% solution had died, and 2 of 10 had died in the 0.001% solution.

EXAMPLE 41

Fungicidal activity of compounds of the present invention is demonstrated by the following tests:

Solutions of compounds of Examples 1 and 13, respectively, were prepared at 1% concentration in distilled water. Further dilutions of 1:100, 1:1000, 1:10,000 and 1:100,000 were made. Cotton gauze was cut into strips about 3 inches wide and folded into squares 6 layers thick. These squares were then dipped into the test solutions and thoroughly wetted. Six pads were treated with each dilution of the two compounds tested, beginning with the greatest dilution. The pads were wrung free of excess solution and inoculated by pressing one surface on the moldy wall of a storage room. They were then folded with the inoculated surface inside, placed in petri dishes, and incubated in darkness at room temperature. All pads were kept moist by adding, when needed, a mildew test solution of nutrient salts comprising 3 gms. of sodium nitrate, 1 gm. of dipotassium phosphate, 0.25 gm. of magnesium sulfate, 0.25 gm. of potassium chloride and sufficient water to give a total volume of 1000 ml.

| Compound of Example No. | Days protection from Mildew at indicated concentration | | | |
|---|---|---|---|---|
| | 1:100 | 1:1000 | 1:10,000 | 1:100,000 |
| Control | | | 8 | |
| 1 | 82 | 57 | 33 | 8 |
| 13 | 55 | 34 | 13 | 13 |

EXAMPLE 42

Inhibition of plant growth utilizing compounds of the present invention is shown by the following tests:

Three week old sunflower plants (Helianthus annuus) were painted, on their cotyledons and primary leaves, with aqueous solutions of varying concentrations of different compounds falling within the scope of this invention. Growth inhibiting effects of such treatments were observed two weeks following treatment and are reported in the following table:

| Compounds of Example No. | Average Plant Height in cm. | | |
|---|---|---|---|
| | 1% | 0.1% | 0.01% |
| Control | | 62 | |
| 1 | — | — | 48 |
| 8 | — | — | 50 |
| 34 | — | 43 | 49 |
| 13 | — | 43 | 54 |
| 2 | 49 | 50 | — |
| 17 | 42 | — | 49 |
| 19 | 48 | — | 51 |

EXAMPLE 43

Lanolin paste formulations containing 1% concentration of various compounds falling within the scope of this invention were applied below the second node of young bean plants (*Phaseolus vulgaris*). Approximately one week after application of the paste formulations, an inspection of the treated plants was made in comparison with control or untreated plants. The percent growth inhibition of the treated plants was determined by measuring the length of the second internodes and comparison with the average lengths of the second internodes of untreated control plants. The reresults are shown below:

| Compound of Example No. | % Inhibition of Plant Growth Relative to Controls |
|---|---|
| 1 | 65 |
| 8 | 78 |
| 13 | 85 |
| 17 | 71 |
| 19 | 78 |
| 26 | 87 |
| 34 | 93 |

From all of the foregoing results it is apparent that the compounds of the present invention display useful agricultural properties such as regulating plant growth and/or controlling fungi and nematodes.

EXAMPLE 44

The compound of Example 36 has proved to be an effective growth regulant. This is dimethyl heptyl (1-hydroxy-p-menth-2-yl) ammonium bromide. This compound and certain other bromides with a different alkyl linkage have proved to be very effective in retarding the second internode of young bean plants as set forth in a publication released May 17, 1968 in *Agricultural and Food chemistry*, Vol. 16, No. 3, pages 523 and 524, May/June 1968 edition. In addition to heptyl bromide, all other bromides starting with ethyl bromide up to octadecyl bromide proved to have growth retardant properties. All these compounds are ethanol soluble and readily soluble in water except the dodecyl and octadecyl derivatives which are only sparingly water soluble.

Test compounds were applied to 7-day-old Black Valentine bean plants at a concentration of 1% in lanolin containing 2.5% Tween-80 (Newhall and Pieringer, *Agricultural and Food Chemistry*, Vol. 14, No. 1, pages 23 to 27, Jan./Feb. 1966 edition). This mixture was applied as a 3 to 5 mm. band around the stem below the second node (Krewson et al, 1959; Newhall and Pieringer, 1966). Treated plants were grown for 7 days, and the lengths of the second internodes were recorded.

A complete test series consisted of the following 13 treatments, each comprising eight bean plants: 11 n-alkyl test compounds, a lanolin-treated control, and an Alar reference. The entire test series was repeated four times at weekly intervals. Growth-retardant activity, determined for each treatment in each series, was statistically analyzed using Duncan's multiple range test to express significance of differences.

The compounds tested are as follows:

a. Dimethyl ethyl (1-hydroxy-p-menth-2-yl) ammonium bromide
b. Dimethyl (1-hydroxy-p-menth-2-yl) ammonium bromide
c. Butyl dimethyl (1-hydroxy-p-menth-2-yl) ammonium bromide
d. Dimethyl (1-hydroxy-p-menth-2-yl) pentylammonium bromide
e. Dimethyl hexyl (1-hydroxy-p-menth-2-yl) ammonium bromide
f. Dimethyl heptyl (1-hydroxy-p-menth-2-yl) ammonium bromide
g. Dimethyl (1-hydroxy-p-menth-2-yl) octylammonium bromide
h. Dimethyl (1-hydroxy-p-menth-2-yl) nonylammonium bromide
i. Decyl dimethyl (1-hydroxy-p-menth-2-yl) ammonium bromide
j. Dimethyl dodecyl (1-hydroxy-p-menth-2-yl) ammonium bromide
k. Dimethyl (1-hydroxy-p-menth-2-yl) octadecylammonium bromide The results of the foregoing test as compared with alar and a control are as follows:

ACTIVITY[a]

| Carbon No. | Series 1 | Series 2 | Series 3 | Series 4 | Over-all[b] | Mean Growth mm.[b] |
|---|---|---|---|---|---|---|
| Ethyl | −39 | −20 | −17 | −6 | −21 | 84.31 |
| Propyl | −29 | −39 | −31 | −23 | −30 | 74.13 |
| Butyl | −51 | −51 | −55 | −40 | −50 | 53.56 |
| Pentyl | −56 | −70 | −65 | −54 | −62 | 40.44 |
| Hexyl | −77 | −84 | −76 | −70 | −77 | 24.31 |
| Heptyl | −78 | −85 | −82 | −73 | −80 | 21.31 |
| Octyl | −70 | −81 | −78 | −65 | −70 | 28.03 |
| Nonyl | −44 | −59 | −52 | −37 | −49 | 54.84 |
| Decyl | −35 | −25 | −19 | −22 | −25 | 79.41 |
| Dodecyl | −1 | −8 | −22 | +2 | −17 | 98.31 |
| Octadecyl | −4 | −12 | −8 | +3 | −5 | 101.03 |
| Alar | −72 | −76 | −79 | −71 | −75 | 26.75 |
| Control | — | — | — | — | — | 106.50 |

[a]Expressed as average per cent reduction (−) or increase (+) in growth as compared to controls.
[b]Expressed as average of 32 measurements.

EXAMPLE 45

As examples of alkyl substituted aralkyl compounds falling within the scope of the invention, the following three compounds are given:

1. Dimethyl (1-hydroxy-p-menth-2-yl) 4-methylbenzylammonium chloride
2. Dimethyl 2,4-dimethylbenzyl (1-hydroxy-p-menth-2-yl) ammonium chloride
3. Dimethyl 2,5-dimethylbenzyl (1-hydroxy-p-menth-2-yl) ammonium chloride The foregoing compounds were applied as an aqueous foliar spray in a volume of 100 gal/A at a rate of 2 lb/A to plants in the two-leaf stage of growth. After a 2 week growth period, the plants were measured and the growth of the treated plants expressed as a percentage of the untreated control (100% means that the treated plants had not grown at all, 0% means that the treated plants were the same size as the controls).

| Compound | Concentration | Growth Inhibition Tomato | Growth Inhibition Black Valentine Bean |
|---|---|---|---|
| 1 | 2.0 lb/A | 20% | 55% |
| 2 | 2.0 lb/A | 80% | 80% |
| 3 | 2.0 lb/A | 80% | 55% |

From the foregoing, it can be seen that substantial growth inhibition is achieved.

EXAMPLE 46

Cyclopentyl dimethyl (1-hydroxy-p-menth-2-yl) ammonium bromide

Five grams of the mixed isomers of 2-dimethylamino-1-p-menthanol were dissolved in 10 ml. of acetone and 10 ml. of cyclopentyl bromide was added. The resulting solution was refluxed for 70 hours. Most of the acetone was removed at reduced pressure using a film evaporator (water bath temperature 50°). Fifty ml. of water were added to the flask and the mixture was transferred to a separatory funnel. The aqueous phase was washed five times with ethyl ether and the ether washes were discarded. Concentration of the neutral, aqueous phase at reduced pressure afforded 1.0 g. (11.5% of theoretical yield) of cyclopentyl dimethyl (1-hydroxy-p-menth-2-yl) ammonium bromide as a colorless, amorphous glass.

Anal. Calc'd for $C_{17}H_{33}NOBr$: N, 4.04. Found: 4.00.

By analogues procedure using cyclohexyl bromide there was also prepared cyclohexyl dimethyl (1-hydroxy-p-menth-2-yl) ammonium bromide.

The foregoing cyclopentyl compound showed growth reduction characteristics in a cucumber seed radicle growth test (4 days) — three replicates of 10 seeds each.

| Treatment | Total Growth (mm.) | % Reduction in Growth |
|---|---|---|
| Control | 722 | — |
| .0005 M | 660 | 8.6 |
| .0002 M | 588 | 18.6 |
| .0001 M | 617 | 14.5 |
| .00005 M | 499 | 30.9 |
| .00002 M | 604 | 16.3 |

As a matter of further information, attention is called to a publication of Newhall and Pieringer in *Agricultural Food and Chemistry*, Vol. 14, No. 1, pages 23 to 27, Jan./Feb., 1966 edition.

EXAMPLE 47

Dimethyl heptyl (1-hydroxy-p-menthan-2-yl) ammonium bromide

Five grams of 2-dimethylamino-1-p-menthanol and 10 g. of heptyl bromide were dissolved in 5 ml. of dimethylformamide. The solution was warmed at 90°C (under nitrogen) for 16 hours, cooled to room temperature and diluted with water (approximately 100 ml.). The mixture was transferred to a separatory funnel and washed three times with ethyl ether (20–25 ml.). The neutral, aqueous phase was concentrated to dryness on a film evaporator (at 50°C). Ninety-five percent ethanol was added to the flask contents to assist the azeotropic removal of water. Last traces of DMF were removed at high vacuum (1 mm.). Yield of dimethyl heptyl (1-hydroxy-p-menthan-2-yl) ammonium bromide was 10.2 g. (100T of theory).

The foregoing compounds may be varied to the further extent of substituting other halides in place of the bromide. In this connection, further substitution for bromide can include sulfates, phosphates, phosphonates, sulfonates and alkanoates of from 1 to 8 total carbon atoms.

Without further elaboration, the foregoing will so fully illustrate by invention that others may, by applying current or future knowledge, readily adapt the same for use under various conditions of service.

What is claimed as the invention is:

1. A method of inhibiting plant growth and promoting fruit abscission which comprises applying to the locus to be treated a plant growth regulating amount of the quaternary ammonium compound (2,4-dichlorobenzyl) dimethyl (1-hydroxy-p-menth-2-yl) ammonium .X wherein X is an acid anion selected from the group consisting of halides, sulfates, phosphates, phosphonates, sulfonates and alkanoates of from 1 to 8 total carbon atoms.

2. A method of inhibiting plant growth and promoting fruit abscission which comprises applying to the locus to be treated a plant growth regulating amount of the quaternary ammonium compound dimethyl 2,4-dimethylbenzyl (1-hydroxy-p-menth-2-yl) ammonium .X, wherein X is an acid anion selected from the group consisting of halides, sulfates, phosphates, phosphonates, sulfonates and alkanoates of from 1 to 8 total carbon atoms.

3. A method of inhibiting plant growth and promoting fruit abscission which comprises applying to the locus to be treated a plant growth regulating amount of the quaternary ammonium compound dimethyl heptyl (1-hydroxy-p-menth-2-yl) ammonium .X wherein X is an acid anion selected from the group consisting of halides, sulfates, phosphates, phosphonates, sulfonates and alkanoates of from 1 to 8 total carbon atoms.

4. The method of claim 1 wherein said compound is dimethyl heptyl (1-hydroxy-p-menth-2-yl) ammonium bromide.

* * * * *

UNITED STATES PATENT OFFICE
CERTIFICATE OF CORRECTION

Patent No. 3,960,539   Dated June 1, 1976

Inventor(s) William F. Newhall

It is certified that error appears in the above-identified patent and that said Letters Patent are hereby corrected as shown below:

The term of this patent subsequent to

October 1, 1992, has been disclaimed.

Signed and Sealed this

Sixth Day of July 1976

[SEAL]

Attest:

RUTH C. MASON
*Attesting Officer*

C. MARSHALL DANN
*Commissioner of Patents and Trademarks*